United States Patent [19]

Pines et al.

[11] 4,031,085

[45] June 21, 1977

[54] PREPARATION OF 3-HYDROXYMETHYL-7β-AMINOADIPOYL-7α-METHOXY-3-CEPHEM-4-CARBOXYLIC ACID

[75] Inventors: Seemon H. Pines, Murray Hill; Matthew A. Kozlowski, South River, both of N.J.

[73] Assignee: Merck & Co., Inc., Rahway, N.J.

[22] Filed: Feb. 17, 1976

[21] Appl. No.: 658,325

Related U.S. Application Data

[63] Continuation of Ser. No. 517,123, Oct. 23, 1974, abandoned.

[52] U.S. Cl. .............................. 260/243 C; 424/246
[51] Int. Cl.² ........................................ C07D 501/02
[58] Field of Search .............................. 260/243 C

[56] References Cited

UNITED STATES PATENTS

| | | | |
|---|---|---|---|
| 3,459,746 | 8/1969 | Flynn | 260/243 C |
| 3,985,742 | 10/1976 | Stapley et al. | 260/243 C |

*Primary Examiner*—Nicholas S. Rizzo
*Attorney, Agent, or Firm*—Edmunde D. Riedl; Julian S. Levitt; Hesna J. Pfeiffer

[57] ABSTRACT

This invention relates to the preparation of 3-hydroxymethyl-7β-aminoadipoyl-7α-methoxy-3-cephem-4-carboxylic acid from 3-(α-methoxy-p-sulfo-oxycinnamoyloxymethyl)-7β-aminoadipoyl-7α-methoxy-3-cephem-4-carboxylic acid or 3-(α-methoxy-p-hydroxycinnamoyloxymethyl)-7β-aminoadipoyl-7α-methoxy-3-cephem-4-carboxylic acid by treatment at 60° C. and pH 3.5–6.5 for about 1 hour. The starting compounds are isolated as fermentation products produced by various Streptomyces species.

2 Claims, No Drawings

PREPARATION OF 3-HYDROXYMETHYL-7β-AMINOADIPOYL-7α-METHOXY-3-CEPHEM-4-CARBOXYLIC ACID

This is a continuation of application Ser. No. 517,123 filed Oct. 23, 1974, now abandoned.

SUMMARY OF THE INVENTION

In brief, this invention provides a rapid and simple method of preparing the compound of the formula

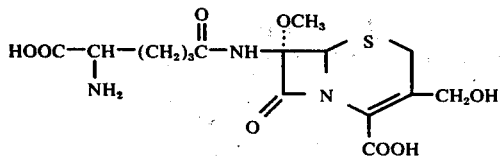

by hydrolysis, under mildly acidic conditions, at moderate temperatures, from compounds of the formula:

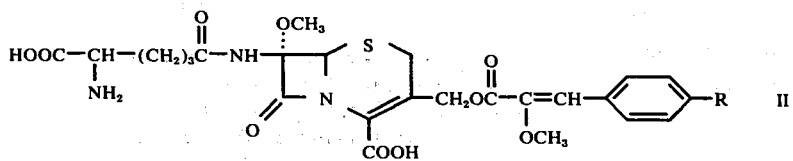

wherein R is hydroxy or sulfo-oxy.

The compound of Formula I has antibacterial activity. It is also useful an an intermediate to make 7α-methoxy cephalosporin compounds which have enhanced gram-negative activity over the des-methoxy analogue. The 3-hydroxymethyl substituent can be derivatized to form, e.g, the 3-carbamoyloxymethyl side chain which is a highly desirable activity-enhancing side chain in the cephalosporin art. In addition, the 7β-aminoadipoyl side chain can be interchanged to form other 7β-acylamido substituents. For instance, the compound of Formula I can be used to prepare 7β-(2-thienylacetamido)-7α-methoxy-3-carbamoyloxy-methyl-3-cephem-4-carboxylic acid, an antibiotic which is highly active against both gram positive and gram negative bacteria.

The starting materials for the process of this invention are described and claimed in co-pending U.S. applications the most recently filed of a series being Ser. No. 463,948, filed Apr. 25, 1974, Stapley and Mata, assigned to Merck & Co., Inc. A foreign patent which is avialable in the literature with the detailed description of the organisms producing the starting materials, the fermentation procedure, and the isolation and recovery steps, is Belgium Pat. No. 764,160. A discussion of the structural determination of these compounds, also known as cephamycin A and cephamycin B (R is sulfo-oxy or hydroxy, respectively) is found in *Tetrahedron Letters*, No. 29, pages 2911–2914, (1972).

The process of this invention takes place using the following general conditions. The starting material of Formula II is dissolved in water, or utilized as an aqueous solution. The pH of the solution is adjusted to between about 3.5 to 6.5, and preferably between about 5 to 6.5 by addition of base, conveniently an alkali metal or alkaline earth metal, hydroxide or carbonate, such as sodium hydroxide or sodium carbonate.

Alternatively, the starting material can be dissolved in an aqueous buffer system which is maintained at a pH between about pH 3.5–6.5. Such systems are known in the art, and include, for instance, the tartrate, phthalate, and phosphate buffers.

In another alternate method of usng the starting material, the crude or partially purified fermentation broth containing either cephamycin A or cephamycin B, or a mixture of both, can also be used directly. The fermentation broth is adjusted to the pH range of between 3.5 and 6.5, treated, and the product recovered.

The solution is heated to between about 60°–70° C for from 30 minutes to 2 hours, and the resulting product is isolated using chromatographic or other techniques.

Yields of the 3-hydroxymethyl product (I) are generally between about 15 and 50%, based on the starting material.

Representative examples are included to demonstrate particular reaction conditions.

EXAMPLE 1

3Hydroxymethyl-7β-aminoadipoyl-7α-methoxy-3-cephem-4-carboxylic acid

A solution of 0.5 grams of cephamycin B (Formula II, above, wherein R is hydroxy) in 25 ml. of water is adjusted to pH 5 with 0.1 N sodium hydroxide. It is heated to between 60°–65° C. and kept at that temperature for 1 hour. The reaction mixture is then cooled, adjusted to pH 1.6 and purified by passing through 8 ml. of Dowex 50-X-12 on the hydrogen cycle, then 20 ml. of IRA 68 on the free base cycle, and eluted with pyridine. The major fraction is recovered at R.f. 029. The freeze-dried solids, weighing 116 mg., are identified, using electrophoresis, and mass spectrographic analysis, as 3-hydroxymethyl-7β-amino-adipoyl-7α-methoxy-3-cephem-4-carboxylate. The yield is calculated as 32%. UV analysis shows a λ max at 263.

EXAMPLE 2

3-Hydroxymethyl-7β-aminoadipoyl-7α-methoxy-3-cephem-4-carboxylic acid

A solution of 0.5 gms. of cephamycin A, (Formula II, above, wherein R is sulfo-oxy in 25 ml. of water to unadjusted pH 5.3 by addition of 0.1N sodium hydroxide. After 45 minutes of heating at 65° C., the product, 3-hydroxymethyl-7β-aminoadipoyl-7α-methoxy-3-cephem-4-carboxylic acid, is recovered, in 19% yield, and identified by comparison with a known standard.

EXAMPLE 3

3-Hydroxymethyl-7β-aminoadipoyl-7α-methoxy-3-cephem-4-carboxylic acid

Cephamycin A (0.5 gm.) is warmed in 20 ml. pH 5.3 phosphate buffer at 65° C. for 45 minutes. The solvent is removed by lyophilization. The residue is chromatographed on Whatman No. 3 paper using 70/30 propanol/water for development. A strong UV absorbing band is found at R.f. 027. It is eluted with water, and identified as the desired 3-hydroxymethyl-7β- aminoadipoyl-7α-methoxy-3-cephem-4-carboxylic acid.

EXAMPLE 4

A fermentation broth prepared by fermentation of *S. griseus*, containing a mixture of cephamycin A and B is subjected to preliminary purification by cooling to 10° C., adjusting to pH 3 with mineral acid, filtered to remove gross impurities, and passed through one-tenth volume of a column containing XAD-2 resin at 3 bed volumes per hour. The broth is washed out of the column with 2 bed volumes of water. The resin, which contains the impure cephamycins A and B, is slurried with 3 bed volumes of water, and adjusted to pH 5.5 by addition of dilute sodium hydroxide. The slurry is heated to and held at 60° C. After 1 hour, the slurry is cooled to 10° C., adjusted to pH 3 and filtered. The water is removed by lyophilization. The resulting solid is identified as 3-hydroxymethyl-7β-aminoadipoyl-7α-methoxy-3-cephem-4-carboxylic acid.

What is claimed is:

1. The process of preparing the compound

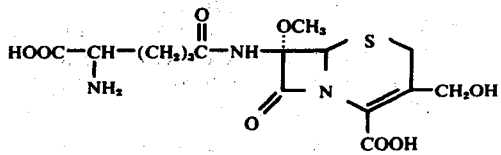

which comprises reacting the compound of the formula

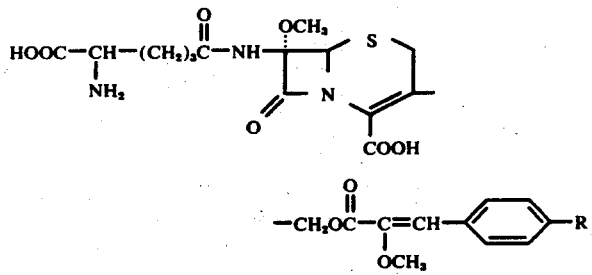

wherein R is hydroxy or sulfo-oxy in an aqueous system at between about pH 3.5–6.5 at 60°–70° C., and recovering the product thereby produced.

2. The process of claim 1 wherein the reaction is complete within 30 minutes to 2 hours.

* * * * *